United States Patent [19]

Biearman

[11] Patent Number: 4,610,245

[45] Date of Patent: Sep. 9, 1986

[54] MEDICAL PROTECTIVE SLEEVE

[76] Inventor: Lorraine Biearman, 2871 Mount Troy Rd., Pittsburgh, Pa. 15212

[21] Appl. No.: 715,358

[22] Filed: Mar. 25, 1985

[51] Int. Cl.$^4$ ............................................. A61F 13/00
[52] U.S. Cl. ..................................... 128/82; 604/179; 128/DIG. 26; 128/133
[58] Field of Search ........... 128/82, 83, 133, DIG. 26, 128/DIG. 6; 604/174, 179, 180

[56] References Cited

U.S. PATENT DOCUMENTS

| | | | |
|---|---|---|---|
| 2,727,512 | 12/1955 | Muller | 128/DIG. 26 |
| 3,059,645 | 10/1962 | Hasbrouck et al. | 128/346 |
| 3,785,374 | 1/1974 | Lipson | 128/82 |
| 3,957,048 | 5/1976 | Jacobs | 128/133 |
| 4,098,268 | 7/1978 | Scott | 128/82 |
| 4,224,935 | 9/1980 | Metelnick | 128/82 |
| 4,346,699 | 8/1982 | Little | 128/82 |
| 4,363,317 | 12/1982 | Broucek | 128/82 |
| 4,397,647 | 8/1983 | Gordon | 604/180 |
| 4,449,975 | 5/1984 | Perry | 604/179 |
| 4,480,639 | 11/1984 | Peterson et al. | 128/207 |
| 4,523,586 | 6/1985 | Couri | 128/82 |

Primary Examiner—Richard J. Johnson
Attorney, Agent, or Firm—Buell, Ziesenheim, Beck & Alstadt

[57] ABSTRACT

A waterproof fabric sleeve or cover for a human limb has a cuff which can be wrapped tightly around the limb. To the inside surface of the cuff is affixed a circumferentially elongated fitting of resilient material thicker at its mid-section than at its ends and having a transverse groove at its mid-section dimensioned to hold an intravenous feeding tube. The groove is open at its inside surface an amount less than its greatest diameter. The sleeve is positioned on the limb so that the intravenous tube fits into the groove and the cuff is wrapped tightly enough to seal it to the limb. The fitting is positioned with a margin of the cuff on each side and the cuff margins seal it to the limb when the intravenous tube is removed.

5 Claims, 3 Drawing Figures

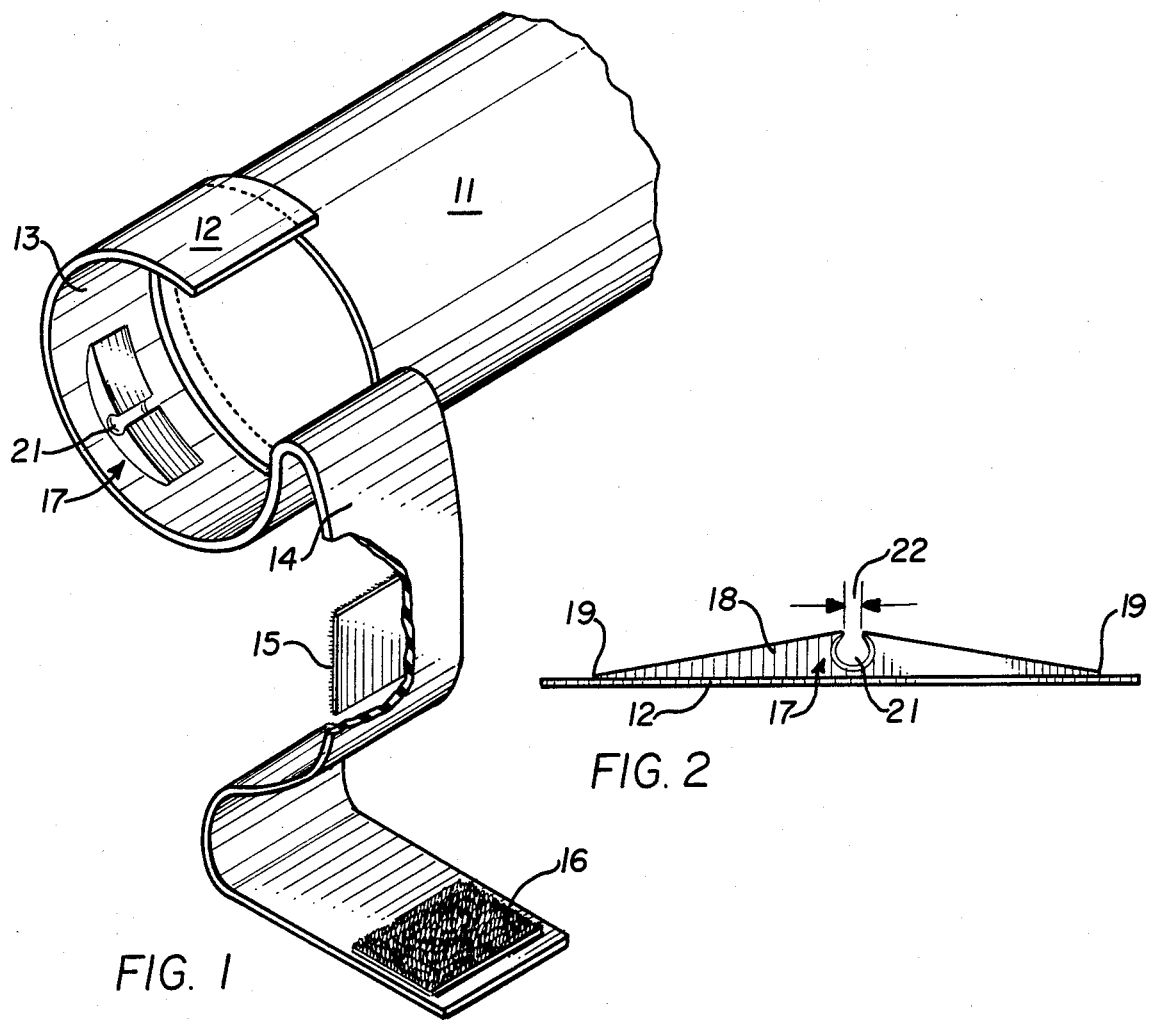
FIG. 1
FIG. 2
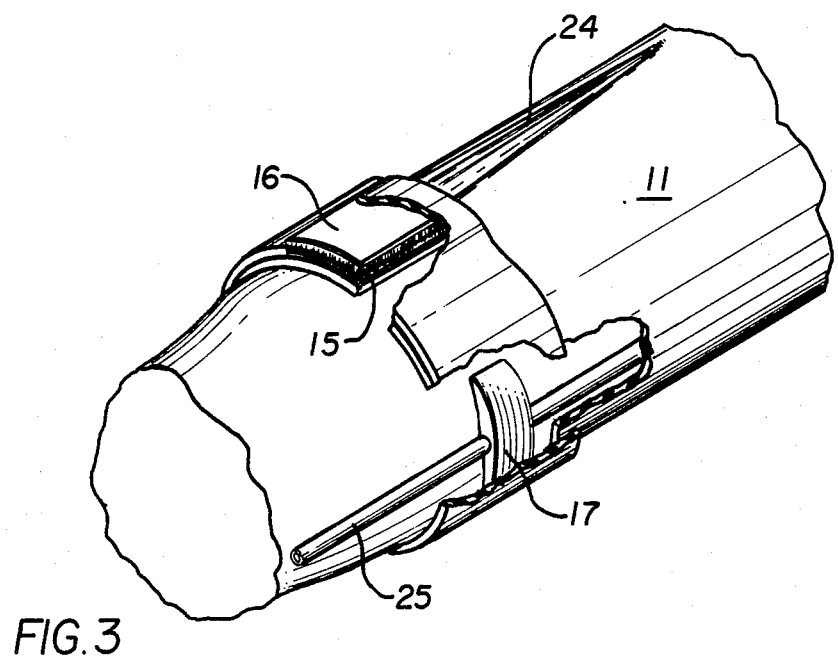
FIG. 3

MEDICAL PROTECTIVE SLEEVE

BACKGROUND OF THE INVENTION

Waterproof protective sleeves or covers for limbs in casts are disclosed in a number of prior patents, particularly Lipson U.S. Pat. No. 3,785,374 of Jan. 15, 1974 and Broucek U.S. Pat. No. 4,363,317 of Dec. 14, 1982. Both of them are concerned with tubular waterproof flexible sleeves or coverings which seal against a limb or cast, the earlier patent with inflatable cuff and the later one with a cuff or bandage with overlapping ends, one end being provided with a stretchable flap. The purpose of such sleeves or covers is, of course, to permit the wearer to bathe without wetting a bandaged limb or a limb treated otherwise, or to protect a plaster cast around a limb. A disadvantage of the sleeves as above-mentioned and all other protective sleeves with which I am familiar is that they cannot be readily used with a patient who is being intravenously fed or medicated.

SUMMARY OF THE INVENTION

My invention to be described in detail hereinafter overcomes the above-mentioned difficulty by providing a sleeve or cover for a limb, in or out of a cast, with a resilient cuff. The cuff carries a fitting which allows an intravenous tube to enter the sleeve at the cuff without destroying the seal which the cuff forms and also allows the tube to be withdrawn while still maintaining the seal. The fitting is an elongated member of resilient material such as rubber, thicker at its middle than at its ends, with a transverse groove fitting an intravenous tube in its middle section. The fitting is preferably affixed to the inside surface of the cuff. The groove is open to a width less than groove width at the fitting surface held against the limb by the cuff. The intravenous tube passes through the groove from outside into the sleeve. The width of the fitting is less than the cuff width, preferably about half. When the intravenous tube is withdrawn the tension in the resilient cuff pulls the cuff margins at each side of the fitting tightly against the limb of the wearer so that the seal between cuff and limb is maintained.

BRIEF DESCRIPTION OF THE DRAWINGS

FIG. 1 is an isometric view of my device attached to a protective sleeve.

FIG. 2 is a side elevation of the fitting of my device which holds the intravenous tube in place on the cuff.

FIG. 3 is an isometric view showing my device in place and pulled tight on a limb.

DESCRIPTION OF MY PREFERRED EMBODIMENT

In FIG. 1 a tubular waterproof fabric sleeve or cover 11 with an open end has a cuff 12 of rubber or other resilient material affixed to its open end so that it projects beyond that end around the major portion of its circumference. The material extending beyond the end of cover 11 forms a margin 13. Cuff 12 has a loose end 14 long enough to encircle sleeve 11. The outside surface of end 14 carries an element 15 of a fastening device and the inside surface of end 14 carries a matching fastening element 16 spaced from element 15 so as to mate with element 15 when cuff end 14 is looped around sleeve 11 on a limb. My preferred fastener is the hook and loop "VELCRO" type but any fastening allowing for adjusting the length of cuff end 14 can be used.

On the inside surface of cuff 12 in margin 13 is positioned a fitting 17 made of natural or synthetic rubber or other resilient material. An elevation of fitting 17 on a portion of cuff 12 laid out flat is shown in FIG. 2. I prefer to affix fitting 17 to cuff 12 but it can be held in place by the tension of the cuff after it is pulled tight around a limb as will be described hereinafter. Fitting 17 is elongated in the circumferential direction of cuff 12. It is made about half the width of margin 13 and positioned about midway between the inner and outer edges of that margin. Its portion 18 intermediate its ends 19 is substantially thicker than ends 19, which may be no thicker than the material of cuff 12. Center portion 18 is thicker than the outside diameter of an intravenous tube. In that center portion is formed a transverse groove 21 which in profile is an arc of a circle dimensioned to grip an intravenous tube. Groove 21 is open at its upper surface over an arc 22 less than the corresponding arc of an intravenous tube and less than the diameter of the groove 21.

In use my sleeve 11 is slipped over the limb with intravenous tube in place thereon. The sleeve is rotated so that the groove 21 in fitting 17 is in line with that tube, which is then pushed into groove 21 through its open arc 22. The material of fitting 17 is sufficiently resilient to accept the tube. The loose end 14 of the cuff is then wrapped around the sleeve 11 and the limb circumferentially, pulled tight and fastened by pressing fastening element 16 against fastening element 15. As is shown in FIG. 3, excess material of sleeve 11 is gathered in the form of longitudinal pleats 24 adjacent the mating fasteners. The intravenous tube 25 is held in fitting 17 against the limb of the patent and the resilient material of fitting 17 seals against tube 25 so that sleeve 11 is watertight. If it is desired to use my sleeve without the intravenous tube that tube is removed. When cover 12 is pulled tight the resilient cuff material overlapping fitting 17 along each side pulls tight enough to seal against the patient's limb and the sleeve remains waterproof.

While I have described my invention hereinabove in connection with a sleeve having one open end, it is equally applicable for sealing both ends of a sleeve having both ends open.

In the foregoing specification I have described a presently preferred embodiment of my invention; however, it will be understood that my invention can be otherwise embodied within the scope of the following claims.

I claim:

1. In a watertight cover for a human limb comprising a sleeve having at at least one end an adjustable length cuff of resilient material and fastening means therefor adapted to form a watertight seal between limb and sleeve the improvement comprising means at that end for positioning an intravenous feeding tube within the sleeve, said means comprising a fitting of resilient material positioned against the inside surface of said cuff, the fitting being elongated in the circumferential direction of the cuff, being thicker intermediate its ends than at its ends and having a transverse slot intermediate its ends open on the inside surface of said fitting to a width less than the width of the slot, said slot being adapted to hold an intravenous tube therein.

2. The apparatus of claim 1 in which the width of the fitting is less than the width of the cuff whereby in the absence of said intravenous tube the tension of the cuff maintains said seal between limb and sleeve around said fitting.

3. The apparatus of claim 1 in which the width of the fitting is about half the width of the cuff.

4. The apparatus of claim 1 in which the width of the opening of said transverse slot in said fitting is about one half the diameter of the slot.

5. The apparatus of claim 1 in which said fitting is affixed to the inside surface of the cuff.

* * * * *